United States Patent
Petrilla

(10) Patent No.: US 7,532,128 B2
(45) Date of Patent: May 12, 2009

(54) POSITION SENSITIVE INDICATOR DETECTION

(75) Inventor: John F. Petrilla, Palo Alto, CA (US)

(73) Assignee: Alverix, Inc.

( * ) Notice: Subject to any disclaimer, the term of this patent is extended or adjusted under 35 U.S.C. 154(b) by 254 days.

(21) Appl. No.: 11/588,038

(22) Filed: Oct. 25, 2006

(65) Prior Publication Data
US 2008/0100464 A1    May 1, 2008

(51) Int. Cl.
*G08B 5/00* (2006.01)

(52) U.S. Cl. .................. 340/815.4; 340/641; 340/679; 436/164; 436/524

(58) Field of Classification Search ............. 340/815.4, 340/373.1, 575, 576, 635, 650, 691.1, 942, 340/641, 679, 5, 143; 324/763; 385/12; 436/164, 524, 514; 422/82.05, 52; 356/319
See application file for complete search history.

(56) References Cited

U.S. PATENT DOCUMENTS

| | | | |
|---|---|---|---|
| 5,136,280 A * | 8/1992 | Heggli | 340/644 |
| 6,342,846 B1 * | 1/2002 | Argentieri | 340/977 |
| 2001/0052860 A1 * | 12/2001 | McMaster | 340/942 |
| 2002/0154315 A1 * | 10/2002 | Myrick | 356/451 |
| 2005/0037510 A1 * | 2/2005 | Sharrock et al. | 436/164 |
| 2005/0221504 A1 * | 10/2005 | Petruno et al. | 436/524 |
| 2006/0001547 A1 * | 1/2006 | Davenport et al. | 340/641 |
| 2006/0240568 A1 * | 10/2006 | Petruno et al. | 436/514 |
| 2006/0275920 A1 * | 12/2006 | Petrilla et al. | 436/514 |
| 2007/0237447 A1 * | 10/2007 | Mozdy | 385/12 |
| 2008/0081002 A1 * | 4/2008 | Petruno et al. | 422/82.05 |
| 2008/0171397 A1 * | 7/2008 | Hardcastle et al. | 436/164 |

* cited by examiner

*Primary Examiner*—George A Bugg
*Assistant Examiner*—Hoi C Lau
(74) *Attorney, Agent, or Firm*—K&L Gates LLP

(57) ABSTRACT

A detector for a test system having multiple indicators uses position sensitive light detection by multiple light detecting elements to produce a measured signal vector. The measured signal vector, which may include fewer components than there are indicators, has a magnitude and a direction that can identify how many and/or which set of the indicators are active. Analysis of the measured vector signal can use vector composition/decomposition techniques.

18 Claims, 2 Drawing Sheets

POSITION SENSITIVE INDICATOR DETECTION

BACKGROUND

Diagnostic test systems commonly employ indicator stripes or zones that change color or provide another visual indication of a test result. Rapid diagnostic test kits, for example, have been developed to detect and indicate the presence of a specific environmentally or biologically relevant species such as a hormone, a drug, a metabolite, a toxin, or a pathogen-derived antigen in a sample. In a common configuration, the sample, which may contain a target species, is applied to a test strip. The sample then flows along the test strip (e.g., through wicking) to indicator zones, where the presence of the target species in detectable quantities causes a change in the optical properties of the indicator.

Several mechanisms for causing detectable changes in the indictors are known. A binding assay, for example, typically uses a labeling substance and a capture zone that acts as an indicator. With a binding assay, the labeling substance binds to any of the target species present in the sample thereby forming a complex. Complexes that may have been formed in the test strip then flow to and are captured in the capture zone, where the labeling substance changes the capture zone in a detectable manner. For example, the labeling substance may contain a substance such as a reflective material, a dye, a fluorescent material, or a quantum dot that collects in the capture zone and produces a visible indicator for the target substance. The presence or absence of a measurable amount of the target species is thus indicated by the presence or absence of visible change in the capture zone.

Some test systems, such as drug test kits for employee screening, may test for multiple target species (e.g., multiple drugs or drug metabolites) and have multiple indicators respectively for the multiple target species. In general, test result evaluation for a multi-indictor test system has required human observation, an expensive detector system that separately measures the indicators, or an imaging system with pattern recognition. Means to distinguish among multiple indicators often depend upon optical differences of the indicators, e.g., fluorescent material of different wavelengths, or different temporal responses to optical stimulation. These bring the expense and complexity of multiple labeling and binding substances, multiple optical sources of stimulation and high speed circuitry. Means to distinguish among different indicator locations often depend upon movement of the test strip or scanning with either a light source or a sensor. These also bring the expense and complexity associated with motion or scanning control. Simpler or lower cost detection systems and methods that are capable of recognizing optical differences in multiple indicators and providing electronic output are thus sought.

SUMMARY

In accordance with an aspect of the invention, a detection system for multiple indicators uses position sensitive light detection to produce a multi-component signal sometimes referred to herein as a signal vector. The signal vector, which may include more or fewer components than there are indicator zones, has a magnitude and a direction that can identify how many and which set of the indicators are active.

One specific embodiment of the invention is a system for detecting states of indicators. The system includes a detector containing multiple light detecting elements. The light detecting elements are arranged relative to the indicators so that light from any of the indicators causes contributions to the component signals respectively output from at least two of the light detecting elements. Further, for each of the indicators, the light from the indicator causes contributions to the component signals corresponding to a base signal vector characteristic of the indicator. An analysis system can be connected to analyze the component signals to identify the state of one or more of the indicators and in particular may perform a vector analysis of a resultant signal vector having the output from the light sensing elements as components.

Another specific embodiment of the invention is a method for detecting states of indicators that emit respective optical signals indicating the states of the indicators. The method includes measuring the optical signals using multiple light detecting elements that are positioned so that the optical signal from any of the indicators causes contributions to component signals respectively output at least two of the light detecting elements. For each of the indicators, the optical signal from the indicator causes contributions to the component signals corresponding to a base signal vector characteristic of the indicator. Analysis of the component signals can then identify the state of one or more of the indicators.

BRIEF DESCRIPTION OF THE DRAWINGS

Use of the same reference symbols in different figures indicates similar or identical items.

DETAILED DESCRIPTION

In accordance with an aspect of the invention, a detector with multiple outputs produces multiple component signals that depend upon relative positions and intensities of incident optical signals from indicators. The active (or inactive) indicators can be identified from characteristics of the component signals. With one evaluation technique, the component signals are considered to form a resultant signal vector having a magnitude and direction in an n-dimensional space where n is the number of component signals. A baseline vector, for example, corresponding to the resultant signal vector when all of the indicators are active, is defined or measured, and a shift of the direction of the resultant signal vector away from the baseline vector indicates changes in the states of the indicators. A change in the magnitude of the resultant signal vector may also indicate the number of indicators that are active or inactive.

The detector outputs are not required to be in one-to-one correspondence with the indicators, and in general, fewer detector outputs can be employed to reduce costs of the detector system while still distinguishing specific combinations of active indicators. While for each indicator pattern there may be an optimum corresponding detector sensor output pattern, in general, arrangements of either are not significantly constrained. The relative positions of detector sensing locations and indicator locations are preferably selected to avoid common symmetries in order to reduce detection ambiguities.

Figure 1A:
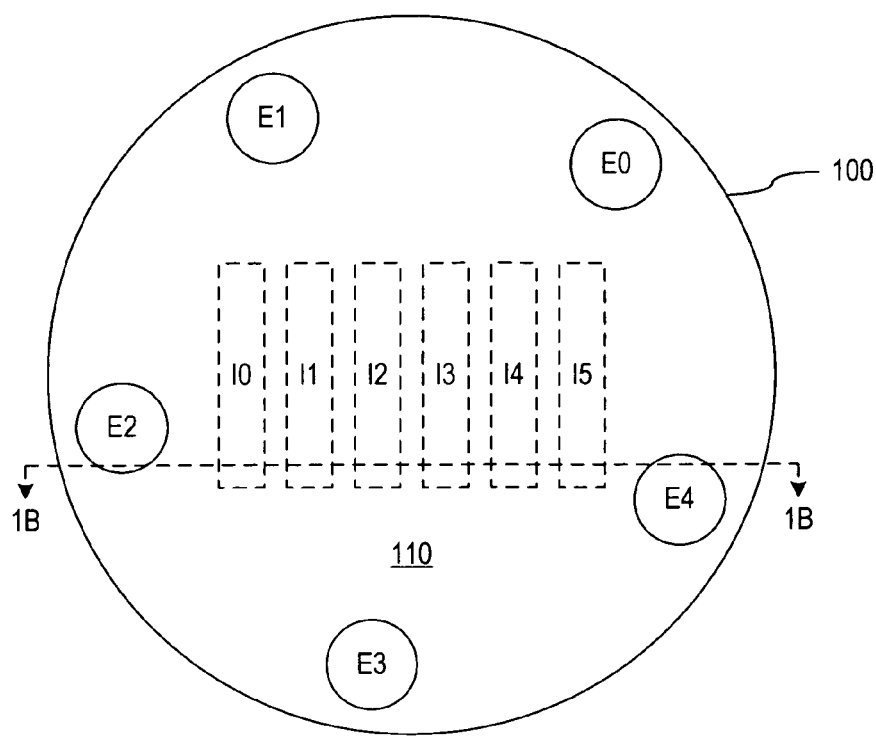
FIGS. 1A, 1B and 1C respectively show a plan view, a cross-sectional view, and a schematic representation of a photo-transistor detector in accordance with an embodiment of the invention in which multiple signal emitters are integrated in a common base region.
Figure 1B:
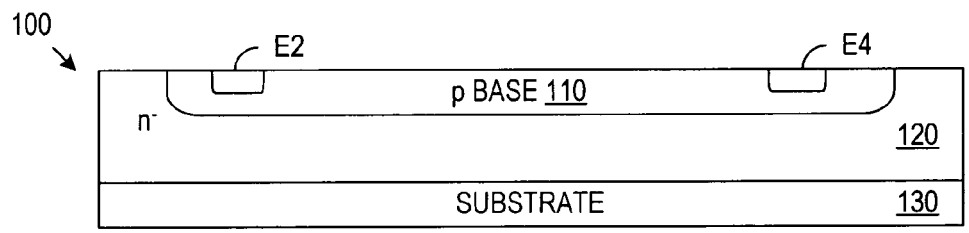

FIG. 1A shows a plan view of a detector 100 in accordance with an embodiment of the invention having multiple emitter regions E0 to E4, and FIG. 1B shows a cross-sectional view for common bipolar silicon integrated circuit embodiment of detector 100. Emitter regions E0 to E4 are in a base area 110, which as shown in the cross-sectional view of FIG. 1B, separates emitter regions E0 to E4 from a collector region 120. In the illustrated embodiment, detector 100 includes five emitter regions E0 to E4 that are equally spaced around the perimeter of a circular area. However, the number and arrangement of emitters in a detector system may vary and be selected according to the number and arrangement of the indicators to be sensed.

In the embodiment of FIG. 1B, emitter regions E0 to E4, base area 110, and collector region 120 are semiconductor material that is doped as required to make detector 100 an NPN photo transistor. In particular, emitter regions E0 to E4 are $n^+$-doped regions, base area 110 is a p-doped region, and collector region 120 is an $n^-$-doped region. An $n^+$-doped buried layer (not shown) may additionally be between base area 110 and collector region 120. Using the same or similar IC process, a PNP photo-transistor detector can be formed using the substrate region as the collector, the n-regions as the base and p regions for emitter sites.

FIG. 1A also shows illumination regions I0 to I5 of base area 110 that are independently subject to being illuminated or not. Illumination regions I0 to I5 on detector 100 are shown as being spatially separated, but in general, each of illumination regions I0 to I5 may partially overlap one or more of the other illumination regions I0 to I5 as long as illumination regions I0 to I5 provide sufficient spatial differentiation. In particular, the shapes and positions of illumination regions I0 to I5 relative to emitter regions E0 to E4 must be such that each of illumination regions I0 to I5 when illuminated will cause a response producing signal levels from emitters E0 to E4 that are characteristic of that illumination region. With such configurations and analysis techniques described further below, active indicators can be detected and distinguished even if the optical signals incident on illumination regions I0 to I5 have the same or indistinguishable optical characteristics. In particular, the optical signals can all have the same frequency spectrum, the same temporal response to optical stimulation, and/or the same polarization, and therefore the indicators can all use the same mechanism and/or labeling substance to indicate test results.

Figure 2:
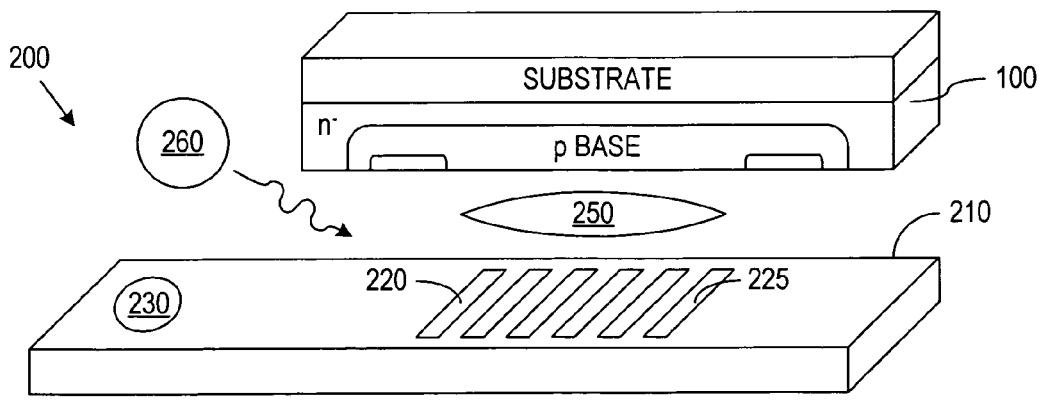
FIG. 2 shows a test system including the detector in accordance with an embodiment of the invention employing the detector of FIGS. 1A, 1B, and 1C.

In an exemplary embodiment of the invention, illumination regions I0 to I5 on detector 100 represent areas of detector 100 that receive light from respective indicators of a test system. FIG. 2, for example, shows a test system 200 including a test strip 210 having six indicators 220 to 225, and illumination regions I0 to I5 respectively correspond to areas on which an optical system 250 projects light from respective indicators 220 to 225.

Test strip 210 in system 200 may be any sort of testing device having separate indicators 220 to 225 that change optical properties, e.g., color, contrast, or brightness, to indicate test results. Many mechanisms for changing the optical character of an indicator are known in the testing field. For example, such indicators can use an analyte-specific binding assay that binds a complex containing a labeling substance and a target species to a zone corresponding to the indicator, and the labeling substance contains a substance such as a reflective material, a dye, a fluorescent material, or a quantum dot that provides a change in the optical properties of the indicator. Alternatively, existence of the target species at a specific level can cause a chemical reaction in a particular indicator to produce a change in the optical properties of the indicator. A lighting system 260 may illuminate or excite indicators 220 to 225 in some manner to produce their respective optical signals, and color filters (not shown) may be used to separate the optical signals from background light. The lighting system 260 may be a simple system that simultaneously illuminates all of indicators 220 to 225 for a measurement, so that a more complex/expensive lighting system that selectively illuminates individual indicators is not required.

In an exemplary embodiment that is described herein as an example, test strip 210 is a lateral flow test strip designed to test for drugs or drug metabolites in urine or other fluid samples. For a drug test, the fluid sample is introduced at a sample introduction area 230 and wicking action in test strip 210 causes the sample to flow laterally to and through indicators 220 to 225. Each indicator 220 to 225 may correspond to a different target species of drug or drug metabolite and undergoes a change in optical characteristics when sample fluid containing the target species enters the indicator. As a definite example, the following assumes that each indictor 220 to 225 has an active or brighter state that corresponds to a negative test result for the target species and an inactive or darker state that corresponds to a positive test for the target species. Accordingly, for the illustrative example, indicators 220 to 225 will all be in the active or brighter state before or at the start of a test, and one or more of indictors 220 to 225 will transition to the inactive or darker state if any of the target species are present in detectable amounts.

Optical system 250 projects light from indicators 220 to 225 respectively onto detector 100, and optical system 250 in general can be any system that receives light from indicators 220 to 225 and illuminates spatially differentiated regions I0 to I5 of detector 100. For example, optical system 250 may include appropriate baffles or other structures (not shown) to block stray light and a lens having object and image planes respectively corresponding to surfaces of test strip 210 and detector 100. (FIG. 2 is not shown to scale because detector 100 would typically be much smaller than test strip 210, and optical system 250 can be used to project light onto the small area of detector 100.) In general, optical system 250 does not require a high quality focusing element to provide spatial differentiation of illumination regions I0 to I5. In fact, focusing in optical system 250 may not be necessary when the spatial separation of indicators provides sufficient spatial differentiation of the illumination regions I0 to I5 and illumination levels are high.

Returning to FIGS. 1A and 1B, emitter regions E0 to E4 are in common base area 110 and at least a portion of each of illumination regions I0 to I4 is on base area 110. Base area 110 and collector 120, which underlies base area 110 as shown in FIG. 1B, can be formed in an epitaxial semiconductor layer formed on an underlying substrate 130 or directly in the material of substrate 130. In particular, a semiconductor material such as silicon, which forms the epitaxial layer or substrate 130, can be doped as required to form bipolar phototransistors having separate emitter regions E0 to E4 and base and collector areas 110 and 120. Other fabrication techniques and structures for phototransistors are known in the art and can alternatively be employed in, for example, detectors having separate emitters with shared or separate base areas and a common collector, or detectors having separate collector areas with shared or separate base areas and a common emitter. Additionally, contact structures and metal interconnections (not shown) can be formed using conventional techniques to enable application of a bias voltage to collector region 120 and output of respective signals from emitter regions E0 to E4. Also not shown are surface passivation layers which can be manipulated for desired optical features, e.g., an anti-reflective layer.

Figure 1C:
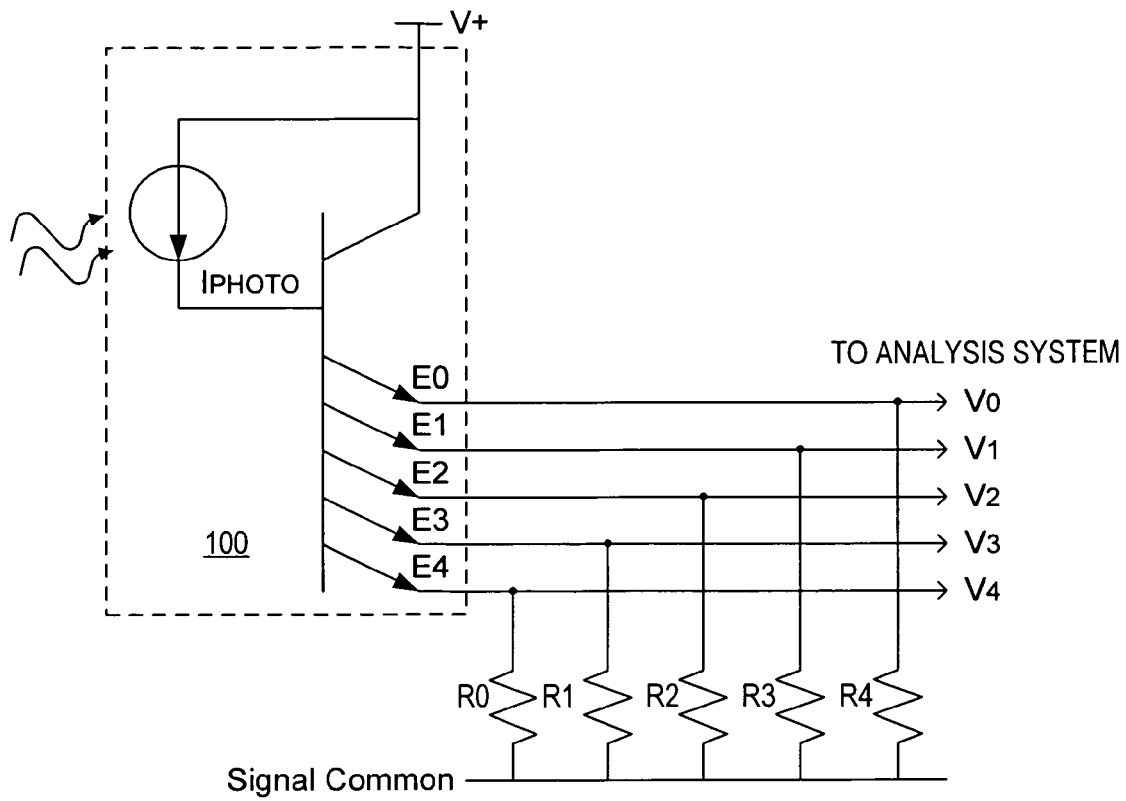

Detector 100 during operation receives one or more optical signals in respective illumination areas I0 to I5. The light is absorbed in detector 100 and creates conduction electrons and holes at depths that depend on the light's wavelength. Light of visible wavelengths can be largely absorbed in the base and collector regions 110 and 120 of an NPN phototransistor. For longer wavelength light the PNP photo-transistor mentioned above may be more effective for light that is absorbed in the substrate. The flow of these carriers, which is shown as photocurrent $I_{PHOTO}$ in FIG. 1C, becomes base current for the phototransistor when detector 100 is biased as shown in FIG. 1C. In the illustrated configuration, a positive bias voltage V+ is applied to collector area 120, and emitter regions E0 to E4 are resistively coupled to a signal common or ground. Resistors R0 to R4, which provide the resistive connection in FIG. 1C, can be replaced by other circuit elements such as trans-impedance amplifiers in alternative embodiments. The respective output voltage V0 to V4 at emitter regions E0 to E4 depend on the intensity of the optical signals and the proximity of illumination areas to respective emitter regions E0 to E4. That is, a closer and more intense optical signal at an emitter region results in a larger current at that emitter, resulting in higher output voltage. An advantage of the phototransistor is that the photo current can be multiplied by the current gain $\beta$ of the transistor and that can lead to significant signal increases at outputs V0 to V4.

Illumination regions I0 to I5 and emitter regions E0 to E4 can be arranged so that each of illumination regions I0 to I5 has a unique combination of distances from emitter regions E0 to E4. With illumination regions I0 to I5 and emitter regions E0 to E4 thus situated, illuminating one of the illumination regions I0 to I5 with the light of from a corresponding active indicator will cause the emitter regions E0 to E4 to conduct signal currents and produce a signal vector that is characteristic of distances to the active illumination region. The characteristic signal vector of each indicator in general may have a limited range of magnitude variation associated with variation in the magnitude of the indicator when active. However, the direction of the characteristic signal vector associated with an illumination region depends on system geometry and can be less dependent of indicator intensity variations. An analysis system (not shown) that is associated with detector 100 stores response signal vectors $V_{I0}$ to $V_{I5}$ respectively for indicators I0 to I5, where each response signal vector has as many components as there are output voltages, e.g., $V_{I0}=[V0_{I0}, V1_{I0}, V2_{I0}, V3_{I0}, V4_{I0}]$, $V_{I1}=[V0_{I1}, V1_{I1}, V2_{I1}, V3_{I1}, V4_{I1}]$, etc. The magnitude and direction of a measured signal vector output from detector 100 can thus be compared to the stored response vectors characteristic of the illumination regions and thereby used to identify a single active indicator.

Multiple active indicators can be similarly identified using vector analysis. In particular, if two or more of the indicators are active, the resultant signal vector-from detector 100 will be a vector sum of the characteristic response vectors associated with the active indicators. Combinations of the characteristic response signal vectors can be evaluated to determine which combination matches the measured result. Whether a unique solution is possible in general depends on the number of emitter regions, the number of indicators, the relative arrangement of the emitter regions, and the intensity variations for active indicators. Unique decompositions of multiple active indicators are possible when sufficient, independent characteristics response vectors are available even when the number of emitter regions is less than the number of indicators since signal vector components can have only positive values and combinations can only be additive. Where a unique vector decomposition is not possible, the magnitude and direction of the signal vector may be used to determine the number of active or inactive indicators.

An alternative technique for evaluating the vector signal output from detector 100 measures a calibration or baseline signal vector corresponding to all of the indicators being active. For example, in an exemplary embodiment where all of the indicators are active to indicate negative test results and are in the active state before a test begins, a baseline vector signal from detector 100 can be measured immediately before the start of a test. A difference between the resultant signal vector from detector 100 and the baseline signal vector will then correspond to subtractions as any of the indictors become inactive, i.e., indicate a positive test result. Additional vector analysis can be applied to the total change in the resultant signal vector from detector 100 to identify how many and/or which indicators became inactive.

Figure 3:
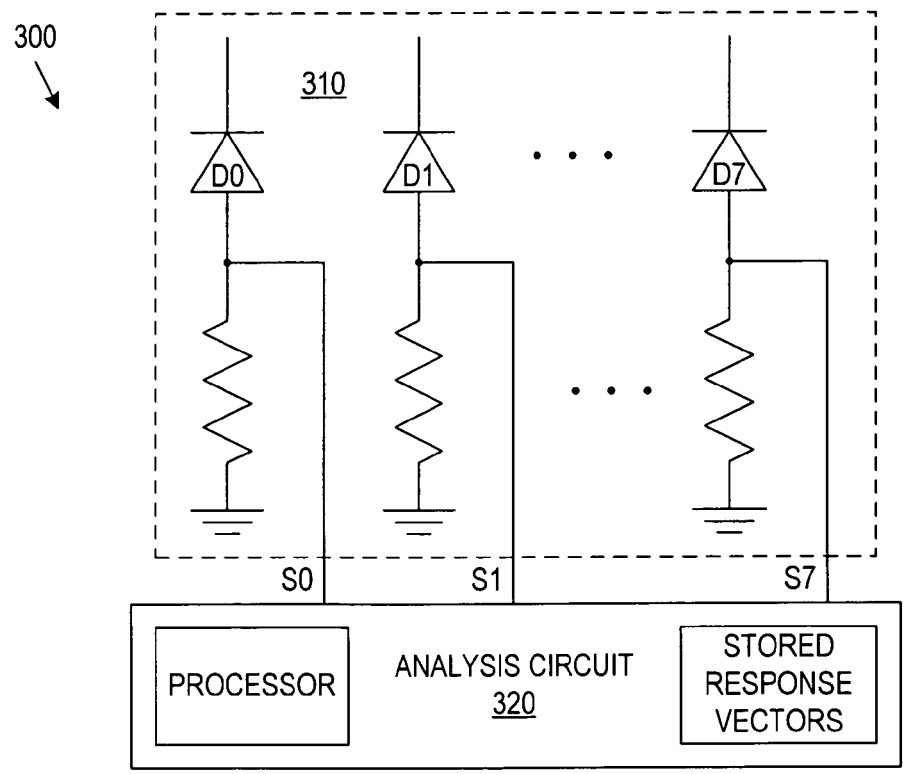
FIG. 3 shows a schematic of a detector system in accordance with an embodiment of the invention employing multiple separate photodiodes.

Principles of the present invention can also be applied to detectors using separate photodiodes or other separate light sensors. FIG. 3, for example, is a block diagram of a system 300 including a detector circuit 310 containing multiple photodiodes D0 to D7. Photodiodes can be positioned asymmetrically relatively to a set of indicators (not shown) or a set of illumination regions associated with indicators. For example, photodiodes D0 to D7 can be positioned so that the set of distances to photodiodes D0 to D7 is unique for each indicator's illumination region. As a result, when any one of the indicators is active, each of photodiodes D0 to D7 produces a corresponding one of signals S0 to S7 at a signal level that depends on the intensity of the active indicator and the distance between the indicator's illumination region and the photodiode. If the set of illumination region-diode distances is unique for each indicator, a signal vector corresponding to component signals S0 to S7 will be unique and characteristic of the indicator.

An analysis circuit 320 is connected to detector circuit 310 and processes electrical signals S0 to S7 to identify a set of active indicators. In particular, analysis circuit 320 can include a memory storing response signal vectors respectively characteristic of the individual indicators and employ and implement the vector analysis processes described above to identify active indicators. The analysis may be either analog, operating directly on the output signal or digital after an A/D conversion of the output signals. Suitable processing for analysis circuit 200 can be implemented using application specific hardware or a microprocessor. Program instructions for an analysis process may be embedded in analysis circuit 320 or accessed from an external location (not shown) and may be recorded on any computer readable medium. In a similar manner an analysis circuit can also be connected to detector circuit 100 of FIGS. 1A, 1B, and 1C.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A system for detecting states of indicators, comprising:
   a detector containing a plurality of light detecting elements that are arranged relative to the indicators so that light from any of the indicators causes contributions to component signals respectively output from at least two of the light detecting elements wherein for each of the indicators, the light from the indicator causes contributions to the component signals corresponding to a signal vector characteristic of the indicator; and an analysis system connected to analyze the component signals to identify the state of one or more of the indicators, wherein the analysis system identifies a set of signal vectors that are respectively characteristic of the indicators and in combination are equivalent to a measured signal vector.

2. The system of claim 1, wherein each of the light detecting elements comprises a separate photodiode.

3. The system of claim 1, wherein each of the light detecting elements comprises a separate emitter region that is in a base area that is common to all of the light detecting elements.

4. The system of claim 1, wherein each of the light detecting elements comprises a phototransistor.

5. The system of claim 1, wherein each of the light detecting elements number fewer than the indicators.

6. The system of claim 1, wherein the analysis system identifies the state of the one or more of the indicators from changes in the component signals relative to corresponding values expected when all of the indicators are active.

7. The system of claim 1, further comprising a test strip on which the indicators reside.

8. The system of claim 7, further comprising an optical system that directs light from the indicators onto the detector.

9. The system of claim 7, further comprising a lighting system that simultaneously illuminates all of the indicators during a measurement by the detector.

10. The system of claim 9, wherein the light detecting elements number fewer than the indicators.

11. The system of claim 10, wherein the indicators have common electro-optical characteristics and differ only by relative position.

12. The system of claim 1, wherein the analysis system stores a plurality of response vectors, each response vector indicating a direction of the signal vector when only a corresponding one of the indicators is in an active state.

13. The system of claim 1, where the analysis system sores an initial vector indicating the signal vector before an operation changes one or more states of the indicators.

14. A method for detecting states of indicators, comprising:

causing the indicators to emit respective optical signals indicating the states of the indicators;

measuring the optical signals using a plurality of light detecting elements, wherein the light detecting elements are positioned so that the optical signal from any of the indicators causes contributions to component signals respectively output from at least two of the light detecting elements, and for each of the indicators, the optical signal from the indicator causes contributions to the component signals corresponding to a signal vector characteristic of the indicator; and analyzing the component signals to identify the state of one or more of the indicators, wherein analyzing comprises identifying a set of signal vectors that are respectively characteristic of the indicators and in combination are equivalent to a measured signal vector.

15. The method of claim 14, wherein analyzing comprises identifying the state of the one or more of the indicators from changes in the component signals relative to corresponding values expected when all of the indicators are active.

16. The method of claim 14, further comprising recording initial values of the component signals before an operation that changes the state of one or more of the indicators, wherein analyzing the component signals detects changes from initial values.

17. The method of claim 14, wherein analyzing the component signals comprises identifying the states of the one or more of the indicators from changes in the component signals relative to corresponding values expected when all of the indicators are active.

18. The method of claim 14, wherein the optical signals all have frequency spectrums that are substantially the same.

* * * * *